(12) United States Patent
Dowaki et al.

(10) Patent No.: US 9,753,267 B2
(45) Date of Patent: Sep. 5, 2017

(54) OBSERVATION SYSTEM, OBSERVATION PROGRAM, AND OBSERVATION METHOD

(71) Applicants: Sony Corporation, Tokyo (JP); Kyoto University, Kyoto-shi, Kyoto (JP)

(72) Inventors: Suguru Dowaki, Kanagawa (JP); Shiori Oshima, Kanagawa (JP); Eriko Matsui, Tokyo (JP); Tatsutoshi Nakahata, Kyoto (JP); Megumu Saito, Kyoto (JP); Akira Niwa, Kyoto (JP)

(73) Assignees: Sony Corporation, Tokyo (JP); Kyoto University, Kyoto (JP)

( * ) Notice: Subject to any disclaimer, the term of this patent is extended or adjusted under 35 U.S.C. 154(b) by 311 days.

(21) Appl. No.: 14/266,383

(22) Filed: Apr. 30, 2014

(65) Prior Publication Data

US 2014/0333723 A1   Nov. 13, 2014

(30) Foreign Application Priority Data

May 10, 2013  (JP) ................................. 2013-100142

(51) Int. Cl.
  *G02B 21/36* (2006.01)
  *G01N 21/65* (2006.01)
(52) U.S. Cl.
  CPC ........... *G02B 21/365* (2013.01); *G01N 21/65* (2013.01)
(58) Field of Classification Search
  CPC .............................. G01N 21/65; G02B 21/365
  See application file for complete search history.

(56) References Cited

U.S. PATENT DOCUMENTS

| 2009/0002702 | A1* | 1/2009 | Maier | A61B 5/417 356/301 |
| 2009/0086314 | A1* | 4/2009 | Namba | G01N 21/6458 359/383 |
| 2010/0251438 | A1* | 9/2010 | Huber | G01N 15/1475 850/1 |
| 2014/0192178 | A1* | 7/2014 | Huang | G02B 21/14 348/79 |

FOREIGN PATENT DOCUMENTS

JP   2012-200156   10/2012

OTHER PUBLICATIONS

Rabut et al., "Automatic real-time three-dimensional cell tracking by fluorescence microscopy" Journal of Microscopy, vol. 216, Pt 2 Nov. 2004, pp. 131-137.*

* cited by examiner

*Primary Examiner* — Mohammed Rahaman
(74) *Attorney, Agent, or Firm* — K&L Gates LLP

(57) ABSTRACT

An observation system includes a microscope optical system, an image pickup unit, an image pickup control unit, a detection unit, and an observation control unit. The image pickup unit is configured to take an image of a field-of-view range of the microscope optical system. The image pickup control unit is configured to cause the image pickup unit to take images of an observation sample in the field-of-view range at a plurality of focal positions and generate detection images. The detection unit is configured to detect a three-dimensional position of an observation target object in the observation sample from the detection images. The observation control unit is configured to fit the field-of-view range of the microscope optical system to the three-dimensional position.

9 Claims, 6 Drawing Sheets

OBSERVATION SYSTEM, OBSERVATION PROGRAM, AND OBSERVATION METHOD

CROSS REFERENCES TO RELATED APPLICATIONS

The present application claims priority to Japanese Priority Patent Application JP 2013-100142 filed in the Japan Patent Office on May 10, 2013, the entire content of which is hereby incorporated by reference.

BACKGROUND

The present disclosure relates to an observation system, an observation program, and an observation method for observing an observation target object by using a microscope.

At a time when an observation target object such as a cell is observed, the observation target object is difficult to be brought into view of a microscope in some cases. In particular, for example, in the case where a floating cell that floats in a culture solution is observed, the cell moves in the culture solution by itself, or the cell is moved due to vibrations or the like associated with a movement of a stage. In this case, a user has to adjust the stage or a focal position and make a search for a desired observation target object while looking at a field of view of the microscope. In particular, when an observation time period becomes longer, the user has to make a search for the observation target object for each predetermined time period, so this task is a heavy burden on the user.

Meanwhile, a technology of tracking a movement of an observation target object by image processing has been developed. For example, Japanese Patent Application Laid-open No. 2012-200156 discloses a cell tracking processing method in which image processing is performed for observation images including a plurality of cells which are taken at predetermined time intervals, and on the basis of morphological characteristics of the cells obtained by analyzing the amount of characteristics, the cells between the observation images are associated.

SUMMARY

However, in the tracking as disclosed in Japanese Patent Application Laid-open No. 2012-200156, it is necessary to observe the observation target object at intervals of several minutes to several tens of minutes. Therefore, there is a fear that the observation target object may be damaged due to phototoxicity. Further, in recent years, a single cell sorting technique has been established in which, on a well plate provided with a plurality of wells, one cell is stored in each of the wells. In the case where wells each store a plurality of cells, the cells have to be tracked and identified. In contrast, in the single cell sorting, cells do not have to be identified, and a placed position of the cell only has to be grasped, thereby making it possible to perform observation.

In view of the circumstances described above, it is desirable to provide an observation system, an observation program, and an observation method capable of making an automatic search for an observation target object.

According to an embodiment of the present disclosure, there is provided an observation system including a microscope optical system, an image pickup unit, an image pickup control unit, a detection unit, and an observation control unit.

The image pickup unit is configured to take an image of a field-of-view range of the microscope optical system.

The image pickup control unit is configured to cause the image pickup unit to take images of an observation sample in the field-of-view range at a plurality of focal positions and generate detection images.

The detection unit is configured to detect a three-dimensional position of an observation target object in the observation sample from the detection images.

The observation control unit is configured to fit the field-of-view range of the microscope optical system to the three-dimensional position.

With this structure, from the detection images which the image pickup control unit causes the image pickup unit to take, the three-dimensional position of the observation target object is detected by the detection unit. The observation control unit fits the field-of-view range of the microscope optical system to the detected three-dimensional position, thereby causing the field-of-view range to match the observation target object. That is, the observation system automatically makes a search for the observation target object. By using the field-of-view range that matches the observation target object, as described above, the observation control unit may perform a detailed observation, or a user may perform the detailed observation.

The image pickup control unit may set a magnification of the microscope optical system to a first magnification and cause the image pickup unit to take an image of the field-of-view range of the microscope optical system.

The observation control unit may set the magnification of the microscope optical system to a second magnification higher than the first magnification and fit the field-of-view range of the microscope optical system to the three-dimensional position.

With this structure, by using the microscope optical system set to the lower magnification (first magnification), the observation system can detect the detection target object from a wide range of the observation sample. By using the microscope optical system set to the higher magnification (second magnification), the user or the observation control unit can perform the detailed observation for the observation target object.

The observation control unit may cause the image pickup unit to take an image of the field-of-view range of the microscope optical system fitted to the three-dimensional position.

With this structure, the image pickup unit takes the image of the field-of-view range that matches the observation target object. The magnification of the microscope optical system is set to the second magnification higher than the magnification (first magnification) at a time when the image pickup control unit causes the image pickup unit to take the detection image, and thus the image taking makes it possible to generate a detailed image of the observation target object.

The observation system may further include an ultraviolet, visible, and infrared light dispersion unit configured to disperse one of ultraviolet light, visible light, and infrared light incident from the microscope optical system.

The observation control unit may cause the ultraviolet, visible, and infrared light dispersion unit to scan the field-of-view range of the microscope optical system fitted to the three-dimensional position.

With this structure, the ultraviolet, visible, and infrared light dispersion unit performs ultraviolet light dispersion, visible light dispersion, or infrared light dispersion for the field-of-view range that matches the observation target object. To perform the dispersion, scanning (line scanning or the like) is necessary. Because the field-of-view range of the microscope optical system matches the observation target object, by scanning the field-of-view range, the observation control unit can perform the dispersion.

The observation system may further include a Raman scattering dispersion unit configured to disperse Raman scattering light incident from the microscope optical system.

The observation control unit may cause the Raman scattering dispersion unit to scan the field-of-view range of the microscope optical system fitted to the three-dimensional position.

With this structure, the Raman scattering dispersion unit performs Raman scattering dispersion for the field-of-view range that matches the observation target object. To perform the dispersion, scanning (line scanning or the like) is necessary. Because the field-of-view range of the microscope optical system matches the observation target object, by scanning the field-of-view range, the observation control unit can perform the dispersion.

The observation sample may be stored in each of a plurality of wells provided in a well plate.

The observation target object may be a cell seeded to each of the plurality of wells of the well plate.

By single cell sorting that uses a flow cytometer, cells can be seeded to the wells of the well plate one by one, respectively. In the case where the cells are seeded to the wells one by one, respectively, it is not necessary to track the cells by tracking. When a substance is detected in the well, the substance can be regarded as the cell. Thus, the observation system according to the present application is particularly suitable to the case where the well plate in which cells are seeded to the wells one by one, respectively, is set as the observation target.

The image pickup control unit may register the well, from which the observation target object is detected by the detection unit, as an observation target well along with the three-dimensional position of the observation target object, and exclude the well, from which the observation target object is not detected by the detection unit, from the observation target well.

With this structure, the well from which the observation target object is detected is registered as the observation target well along with the three-dimensional position, so it is possible to use the three-dimensional position registered in a previous observation to take an image of the detection image. Further, the well from which the observation target object is not detected is excluded from the observation target well, so it is possible to stop a subsequent observation and prevent a wasteful observation.

The image pickup control unit may perform a time-lapse image taking for the observation target well.

In the case of the time-lapse image taking in which image taking is continuously performed at predetermined time intervals, the three-dimensional position of the observation target object and the observation target well obtained from a preceding observation are used, with the result that an efficient observation of the observation target object can be performed.

The observation system may further include an identifier read unit and an identifier management unit.

The identifier read unit is configured to read an identifier of the well plate from an identification marker provided to the well plate.

The identifier management unit is configured to check the identifier supplied from the identifier read unit against an identifier of a well plate which has been previously observed and supplies observation data of the well plate corresponding to the supplied identifier to the image pickup control unit.

With this structure, when the image pickup control unit takes the detection image, it is possible to refer to previous observation data for each well plate. Specifically, the image pickup control unit can omit taking of the detection image for the well excluded from the observation target well in the previous observation, or cause an image of only the vicinity of the three-dimensional image of the observation target object detected in the previous observation to be taken.

According to another embodiment of the present application, there is provided an observation program causing a computer to function as an image pickup control unit, a detection unit, and an observation control unit.

The image pickup control unit is configured to cause an image pickup unit that takes an image of a field-of-view range of a microscope optical system to take images of an observation sample in the field-of-view range at a plurality of focal positions and generate detection images.

The detection unit is configured to detect a three-dimensional position of an observation target object in the observation sample from the detection images.

The observation control unit is configured to fit the field-of-view range of the microscope optical system to the three-dimensional position.

According to another embodiment of the present application, there is provided an observation method including causing, by an image pickup control unit, an image pickup unit that takes an image of a field-of-view range of a microscope optical system to take images of an observation sample in the field-of-view range at a plurality of focal positions and generate detection images.

A three-dimensional position of an observation target object in the observation sample is detected from the detection images by a detection unit.

The field-of-view range of the microscope optical system is fitted to the three-dimensional position by an observation control unit.

As described above, according to the present application, it is possible to provide the observation system, the observation program, and the observation method capable of making an automatic search for the observation target object.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

DETAILED DESCRIPTION

Structure of Observation System

Figure 1:
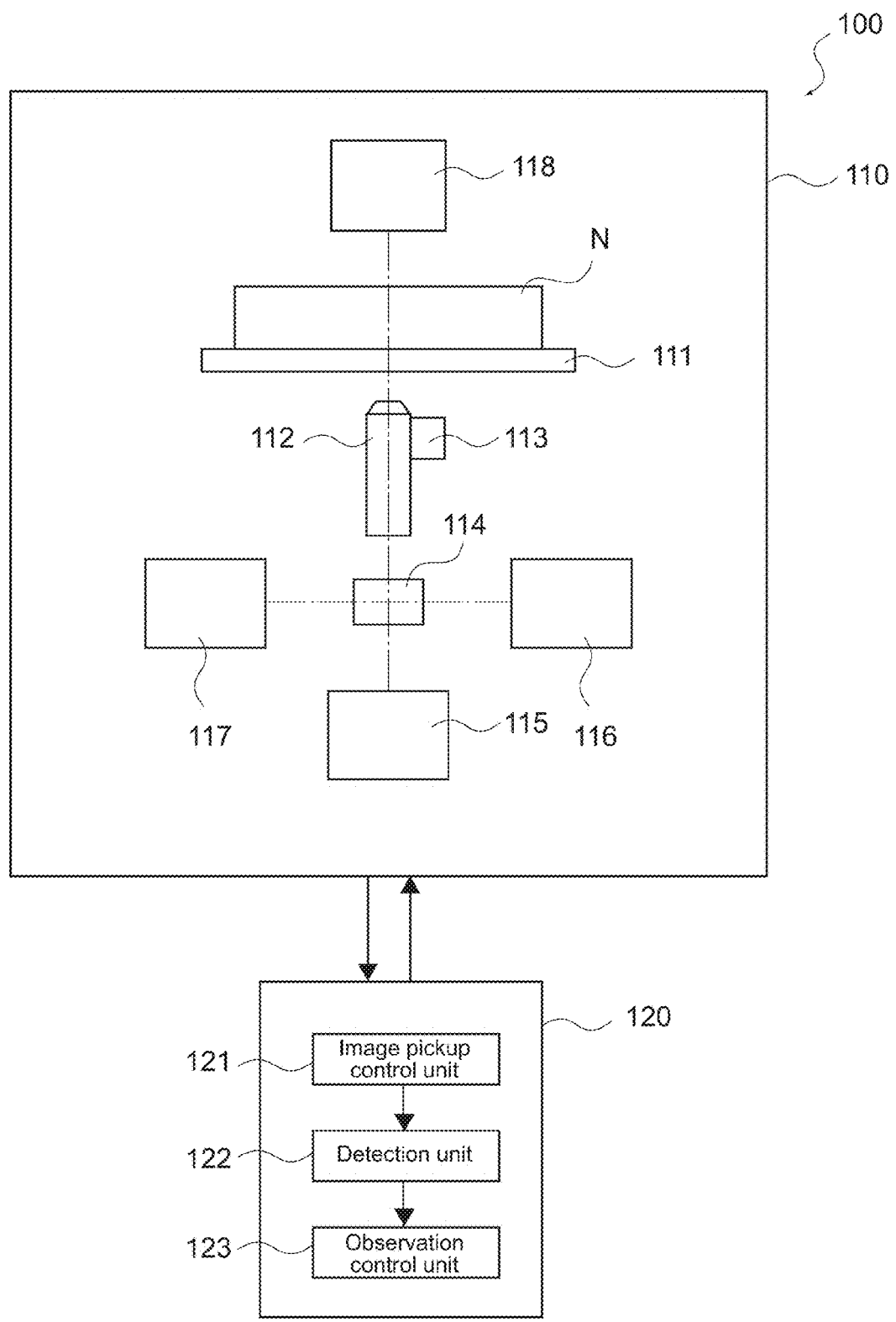
FIG. 1 is a schematic diagram showing the structure of an observation system according to an embodiment of the present application.

FIG. 1 is a schematic diagram showing an observation system according to this embodiment. As shown in the figure, an observation system 100 is constituted of a microscope unit 110 and a control unit 120. The control unit 120 may be integrally formed with the microscope unit 110 or may be an information processing apparatus independently of the microscope unit 110.

The microscope unit 110 includes a stage 111, a microscope optical system 112, an automatic focusing mechanism 113, an optical path switching unit 114, an image pickup unit 115, an ultraviolet, visible, and infrared light dispersion unit 116, a Raman scattering dispersion unit 117, and a transmission lighting 118. Further, on the stage 111, an incubator N is placed.

The stage 111 supports the incubator N and defines a relative position between the incubator N and the microscope optical system 112. The stage 111 can be an X-Y stage movable in a horizontal direction (X-Y direction) by a drive source such as a motor. Further, the stage 111 may be movable in a vertical direction (Z direction) in addition to the horizontal direction. By being controlled by the control unit 120, the stage 111 can move the position relative to the microscope optical system 112.

Figure 2:
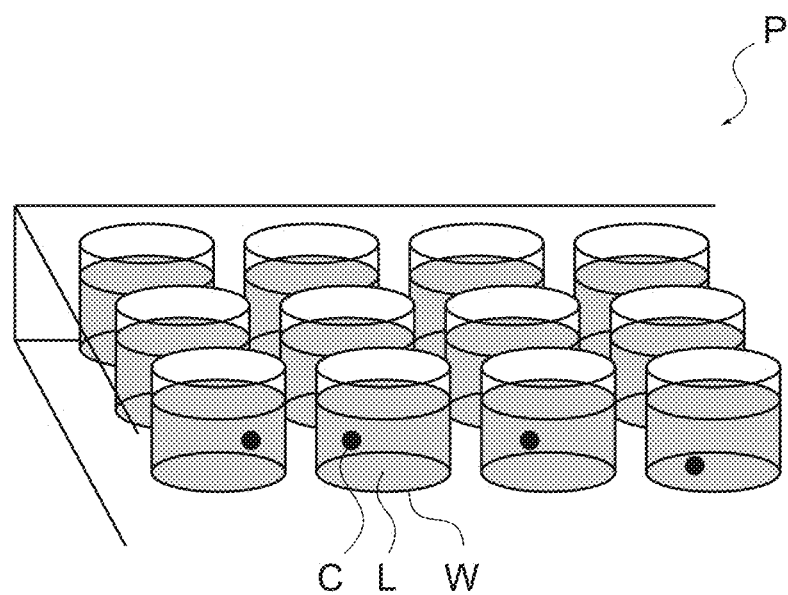
FIG. 2 is a schematic diagram showing of a well plate to be observed by the observation system.

The incubator N stores a well plate that contains an observation target object (cell or the like) therein and can perform various observations with an incubation environment maintained. FIG. 2 is a schematic diagram showing a well plate P. As shown in the figure, the well plate P includes a plurality of wells W. In each of the wells W, an observation sample L containing an observation target object C is stored. The observation target object C can be a cell seeded one by one into each of the wells W by single cell sorting, and the observation sample L can be a cell culture solution.

The microscope optical system 112 is provided with various lenses such as an objective lens and a diaphragm. The microscope optical system 112 increases light (including ultraviolet light and infrared light) that is transmitted through the observation sample or generated on the observation sample and causes the light to enter the optical path switching unit 114. It is desirable that the microscope optical system 112 can perform change to a plurality of magnifications such as a first magnification and a second magnification to be described later.

The automatic focusing mechanism 113 adjusts the focal position of the microscope optical system 112. Specifically, by being controlled by the control unit 120, the automatic focusing mechanism 113 adjusts a distance between the objective lens and the stage 111 and an interval between the various lenses, thereby moving a focal position of the microscope optical system 112 in the Z direction. It is desirable that the automatic focusing mechanism 113 can move the focal position of the microscope optical system 112 so that a Z-Stack image (image taken while moving the focal point in the Z direction) can be taken.

The optical path switching unit 114 distributes light that exits the microscope optical system 112 toward the image pickup unit 115, the ultraviolet, visible, and infrared light dispersion unit 116, and the Raman scattering dispersion unit 117 at predetermined percentages. Further, the optical path switching unit 114 can also distribute incident light at a predetermined percentage toward any one of or two or more of the image pickup unit 115, the ultraviolet, visible, and infrared light dispersion unit 116, and the Raman scattering dispersion unit 117, to be used to observe the observation target object. Furthermore, the optical path switching unit 114 causes excitation light for Raman scattering observation which exits the Raman scattering dispersion unit 117 to enter the microscope optical system 112.

The image pickup unit 115 takes a microscope image of the observation sample with the microscope optical system 112. The image pickup unit 115 is provided with an image pickup element such as a CCD (charge coupled device) image sensor and a CMOS (complementary metal oxide semiconductor) image sensor and can take an image of the observation sample. In accordance with the structures of the microscope optical system 112, the transmission lighting 118, and the like, the image pickup unit 115 can take all or at least one of a bright-field image, a dark-field image, a phase difference image, a fluorescent image, a polarization microscope image, and the like.

The ultraviolet, visible, and infrared light dispersion unit 116 disperses ultraviolet light, visible light, or infrared light that is transmitted through the observation sample. The ultraviolet light, the visible light, or the infrared light emitted from the transmission lighting 118 is transmitted through the observation sample, magnified at a predetermined magnification by the microscope optical system 112, and is guided to the ultraviolet, visible, and infrared light dispersion unit 116 by the optical path switching unit 114. The ultraviolet, visible, and infrared light dispersion unit 116 can generate a two-dimensional spectral image in a ultraviolet region, a visible region, or an infrared region of the observation sample from the ultraviolet light, the visible light, or the infrared light, and can generate an absorption spectrum (ultraviolet, visible, or infrared light dispersion spectrum) of the ultraviolet light, the visible light, or the infrared light from the two-dimensional spectral image. The ultraviolet, visible, or infrared light dispersion spectrum is a plot of absorbance with respect to the wavelength of the ultraviolet light, the visible light, or the infrared light that is transmitted through the observation sample and includes information relating to characteristics (molecular structure or chemical condition) of the observation sample.

It should be noted that the ultraviolet, visible, and infrared light dispersion unit 116 only has to obtain the absorption spectrum in at least one of the ultraviolet, visible, and infrared regions or may obtain the absorption spectrum in all regions of the ultraviolet, visible, and infrared regions. Further, the ultraviolet, visible, and infrared light dispersion unit 116 can also obtain fluorescent ultraviolet, visible, or infrared light dispersion spectrum by performing fluorescent labeling with respect to the observation sample in advance.

The Raman scattering dispersion unit 117 disperses Raman scattering light generated in the observation sample. Specifically, the Raman scattering dispersion unit 117 irradiates the observation sample with excitation light (laser light) having a specific wavelength through the microscope optical system 112. Raman scattering light thus emitted from the observation sample is guided to the Raman scattering dispersion unit 117 through the microscope optical system 112.

From incident Raman scattering light, the Raman scattering dispersion unit 117 can generate a two-dimensional spectral image of the Raman scattering caused by the observation sample, and can generate a Raman scattering spectrum (Raman spectrum) from the two-dimensional spectral image. A wavelength shift (Raman shift) of the Raman scattering light differs depending on characteristics (molecular structure or crystal structure) of the observation sample. That is, the Raman spectrum includes information relating to characteristics of the observation sample.

The transmission lighting 118 emits illumination light to the observation sample. As described above, the image pickup unit 115 can take all or at least one of the bright-field image, the dark-field image, the phase difference image, the fluorescent image, the polarization microscope image, and the like, and the transmission lighting 118 can irradiate the observation sample with light corresponding thereto. In addition, the transmission lighting 118 can irradiate the observation sample with the ultraviolet light, the visible light, the infrared light, or the like as described above.

(Structure and Operation of Control Unit)

Figure 3:
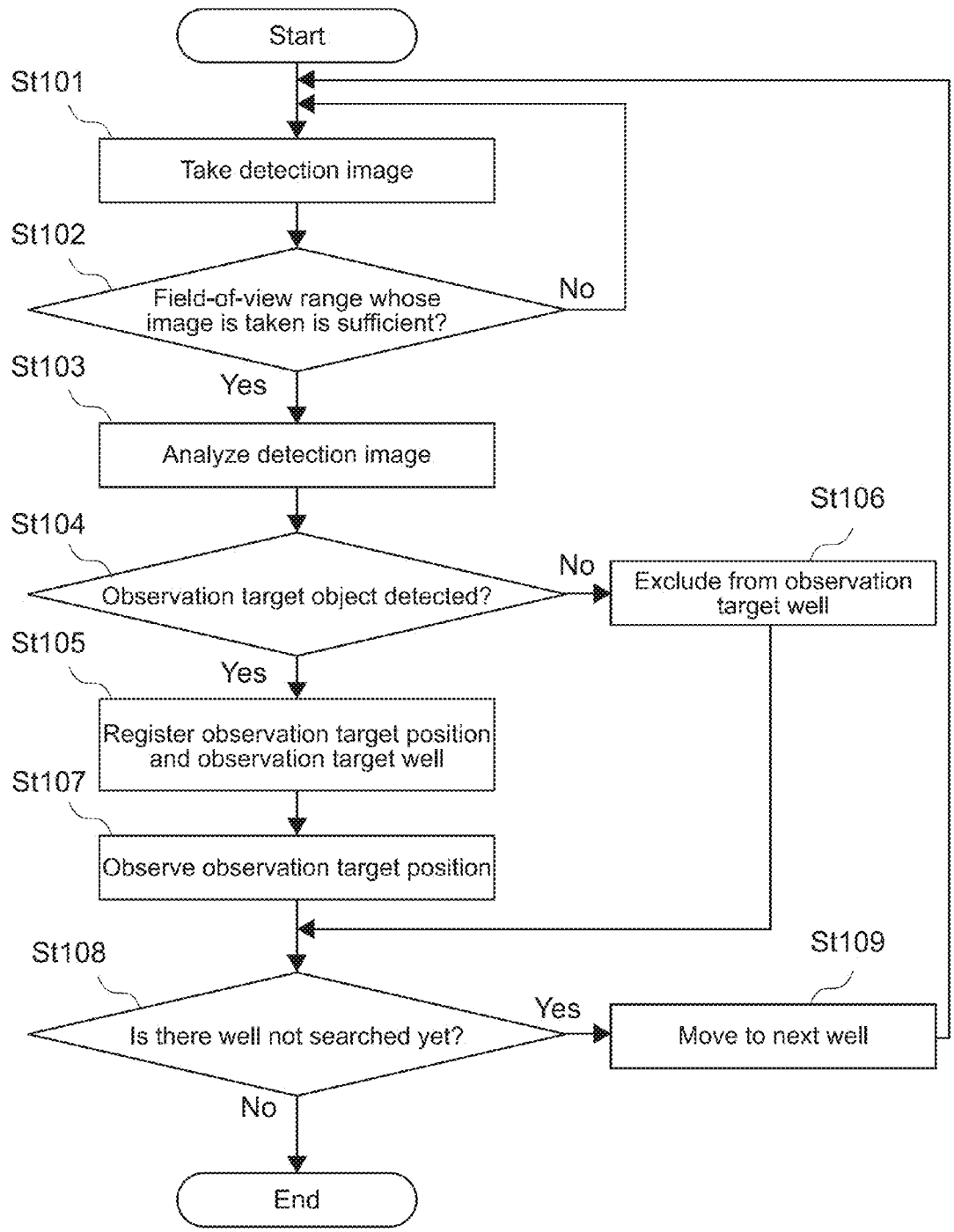
FIG. 3 is a flowchart showing an operation of the observation system.

The control unit 120 controls respective portions of the microscope unit 110. FIG. 3 is a flowchart showing an operation of the control unit 120. As shown in FIG. 1, the control unit 120 includes an image pickup control unit 121, a detection unit 122, and an observation control unit 123.

The image pickup control unit 121 causes the image pickup unit 115 to take images of the observation sample at a plurality of focal positions and generate detection images (St101). Specifically, the image pickup control unit 121 controls the image pickup unit 115, the automatic focusing mechanism 113, the stage 111, and the like to set a field-of-view range of the microscope optical system 112 in a specific well and set the magnification of the microscope optical system 112 to a predetermined magnification (as the first magnification).

Figure 4:
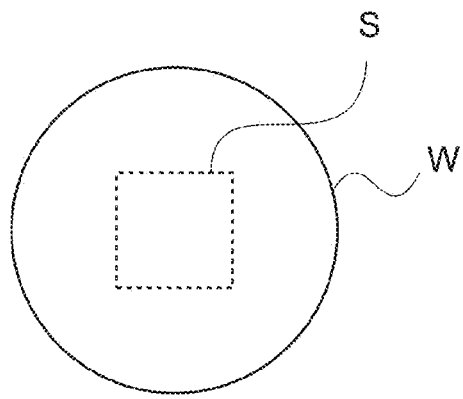
FIG. 4 is a schematic diagram showing a size of a range of a field of view of a microscope optical system of the observation system with respect to a well.
Figure 5:
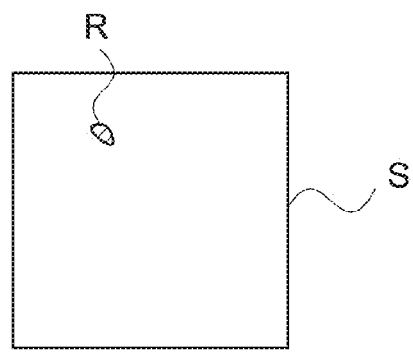
FIG. 5 is a schematic diagram showing the range of the field of view of the microscope optical system of the observation system at a time when a detection target image is taken.

Here, the field-of-view range of the microscope optical system 112 is determined by a size of an imager of the image pickup unit 115 and the magnification (first magnification) of the microscope optical system 112. FIG. 4 is a schematic diagram showing an example of a size of a field-of-view range S of the microscope optical system 112 and the well W. For example, in the case where a CCD image sensor of ⅔ inch (8.8 mm×6.6 mm) is provided to the image pickup unit 115, and the magnification of the microscope optical system 112 is 4×, the field-of-view range S is 2.2 mm×1.65 mm. Here, in the case where the well plate P is a 96 well micro plate, an inner diameter of a bottom surface is approximately ϕ6.4 mm, so the field-of-view range S is smaller than the size of the well W. FIG. 5 is a schematic diagram showing an observation target object R (cell or the like) in the field-of-view range S at this time.

The image pickup control unit 121 causes the image pickup unit 115 to take an image of the observation sample while moving the focal position of the microscope optical system 112 in the Z direction by the automatic focusing mechanism 113 and generate Z-Stack images of the observation sample in the field-of-view range. It should be noted that the image pickup control unit 121 may take the image of the observation sample at a plurality of focal positions by moving the stage 111. Hereinafter, the images of the observation sample taken at the plurality of focal positions, such as the Z-Stack images, are set as the detection images.

In the case where the field-of-view range of the microscope optical system 112 is smaller than the well, the image pickup control unit 121 takes the detection image for one field-of-view range, then moves the field-of-view range S to an area in the well W, an image of which is not yet taken, and can cause the detection image thereof to be taken. In this way, the image pickup control unit 121 can take the detection images for the entire area of the well.

It should be noted that, in the case where the position of an observation target object does not vary, for example, in the case where sorting accuracy of a flow cytometer is high, it is not always necessary to take images of the entire area of the well, and it may be sufficient to take an image of the center of the well in only one field of view. In this case, the image pickup control unit 121 causes an image of only one field of view on the center of the well to be taken and causes the detection image to be generated.

In this way, in the case where the field-of-view range for which the detection image is obtained is not sufficient with respect to the size of the well (No in St102), the image pickup control unit 121 causes the field-of-view range to be moved to an area, an image of which is not yet taken, and causes the image pickup unit 115 to take the detection image again (St101). On the other hand, in the case where the field-of-view range for which the detection image is obtained is sufficient with respect to the size of the well (Yes in St102), the image pickup control unit 121 supplies the detection image obtained from the image pickup unit 115 to the detection unit 122.

The detection unit 122 analyzes the detection image (St103). Specifically, the detection unit 122 uses pattern matching or outline extraction by an edge filter to analyze a detection target image, thereby detecting the observation target object. It should be noted that when the detection images are taken for a plurality of field-of-view ranges in one well, each of the detection images is analyzed.

In the case where only one observation target object is stored in each of the wells, by the single cell sorting or the like as described above, the detection unit 122 detects one observation target object for each well or not. When the detection unit 122 detects the observation target object from the detection image (Yes in St104), the detection unit 122 supplies a three-dimensional position (hereinafter, referred to as observation target position) of the detected observation target object to the observation control unit 123.

Further, the detection unit 122 notifies the image pickup control unit 121 of the observation target position, and the image pickup control unit 121 registers the observation target position with the well from which the detection is performed (hereinafter, referred to as observation target well) (St105). On the other hand, in the case where the detection unit 122 does not detect the observation target object from the detection image (No in St104), the detection unit 122 notifies the image pickup control unit 121 of the well in which the detection image is taken. Thus, the image pickup control unit 121 excludes the well from the observation target well (St106).

Figure 6:
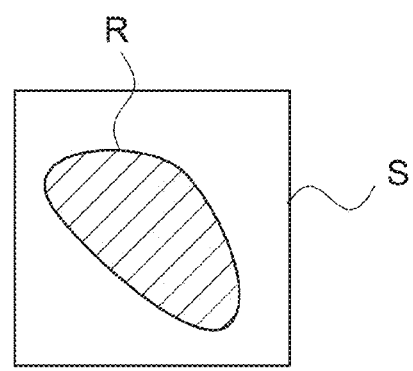
FIG. 6 is a schematic diagram showing the range of the field of view of the microscope optical system at a time of observation by the observation system.

The observation control unit 123 causes the image pickup unit 115, the ultraviolet, visible, and infrared light dispersion unit 116, or the Raman scattering dispersion unit 117 to observe the observation sample on the basis of the observation target position supplied from the detection unit 122 (St107). Specifically, the observation control unit 123 sets the magnification of the microscope optical system 112 to a second magnification, which is higher than the first magnification at a time of taking the detection image, and adjusts the microscope optical system 112 in such a manner that the observation target position corresponds to the center of the field-of-view range of the microscope optical system 112. As a result, the field-of-view range of the microscope optical system 112, which is magnified at the high magnification, is fitted to the observation target object. FIG. 6 is a schematic diagram showing the observation target object R in the field-of-view range S at this time.

In the case where the observation target object is observed by using the image pickup unit 115, the observation control unit 123 controls the optical path switching unit 114 to switch the optical path toward the image pickup unit 115. The observation control unit 123 can increase the magnification of the microscope optical system 112, reduce a depth of field, and cause a microscope image to be taken at a high magnification. Further, the observation control unit 123 performs autofocusing or the like by a contrast detection system, thereby analyzing a Z position with higher accuracy. After that, the observation control unit 123 may perform morphology observation of the observation target object in detail at the high magnification.

In addition, the observation control unit 123 controls the optical path switching unit 114 to switch the optical path toward the ultraviolet, visible, and infrared light dispersion unit 116 and controls the ultraviolet, visible, and infrared light dispersion unit 116 to scan the field-of-view range, with the result that an infrared absorption spectrum can be generated. Further, the observation control unit 123 controls the optical path switching unit 114 to switch the optical path to the Raman scattering dispersion unit 117 and controls the Raman scattering dispersion unit 117 to scan the field-of-view range, with the result that a Raman scattering spectrum can be generated.

It should be noted that the observation control unit 123 may only fit the field-of-view range of the microscope optical system 112 set to the second magnification to the observation target object. As a result, by using the field-of-view range fitted to the observation target object, the user can observe the observation target object with the image pickup unit 115, the ultraviolet, visible, and infrared light dispersion unit 116, and the Raman scattering dispersion unit 117.

In the case where there is a well which is not searched yet (steps subsequent to taking of the detection image) on the well plate P (Yes in St108), the image pickup control unit 121 moves the field-of-view range of the microscope optical system 112 to the well (St109) and executes the steps. On the other hand, in the case where there is no well which is not searched (No in St108), the image pickup control unit 121 terminates the operation.

In the case where the observation target object is observed at predetermined time intervals (time-lapse observation), the image pickup control unit 121 causes the detection image for each well to be taken again and performs the detection of the observation target object by the detection unit 122 and the observation by the observation control unit 123. Here, as described above, because the well from which the observation target object is not detected is excluded from the observation target well, the image pickup control unit 121 is prevented from causing an image of the well where the observation target object does not exist to be taken wastefully.

In addition, in the case where the field of view of the microscope optical system 112 is narrow relative to the size of the well or in the case where a stroke of the automatic focusing mechanism 113 is short, in the second image taking and thereafter, the image pickup control unit 121 causes the detection image mainly for the observation target position (see, St105) previously registered to be taken, thereby making it possible to reduce the image taking counts for one well.

As described above, in the observation system, the image pickup control unit 121 takes the detection image, and the detection unit 122 detects the observation target object from the detection image, with the result that the observation control unit 123 can observe the observation target object. As a result, it is unnecessary to make the search for the observation target object in the observation sample by the user, so an efficient observation can be performed. In addition, in the observation system, unlike the tracking technique in related art, it is unnecessary to perform irradiation with light for a long time period, and it is possible to prevent the phototoxicity with respect to the observation target object.

(About Automatic Identification of Well Plate)

As described above, the well plate is stored in the incubator N (see, FIG. 1), and the observation can be performed while cultivating the observation target object (cell or the like). However, in the case where an observation time period is long, for example, in the case of a time-lapse observation, one well plate occupies the observation system, so it may be impossible to use the observation system for another observation. For this reason, at timing when a single observation of the time-lapse observation is terminated, the well plate may be moved to another incubator.

In the case where there are a plurality of well plates as described above, it is necessary to identify the well plates. It is desirable that the observation system can automatically identify the well plates as follows. It should be noted that identification markers including identifiers of the well plates, such as barcodes and handwritten makers by a user, are provided in advance to the well plates, respectively.

Figure 7:
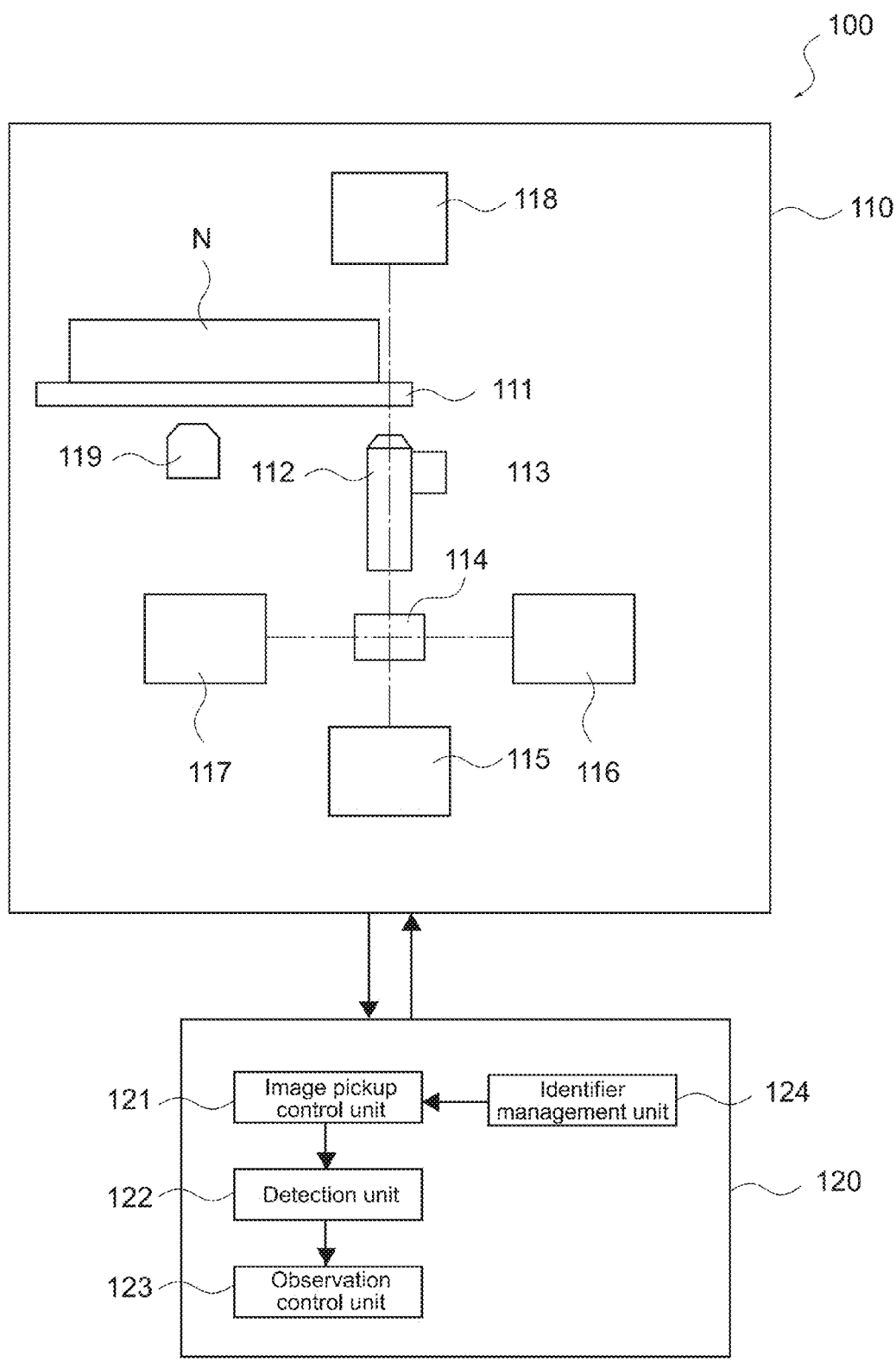
FIG. 7 is a schematic diagram showing the structure of the observation system having a well plate identification function according to the embodiment of the present application.
Figure 8:
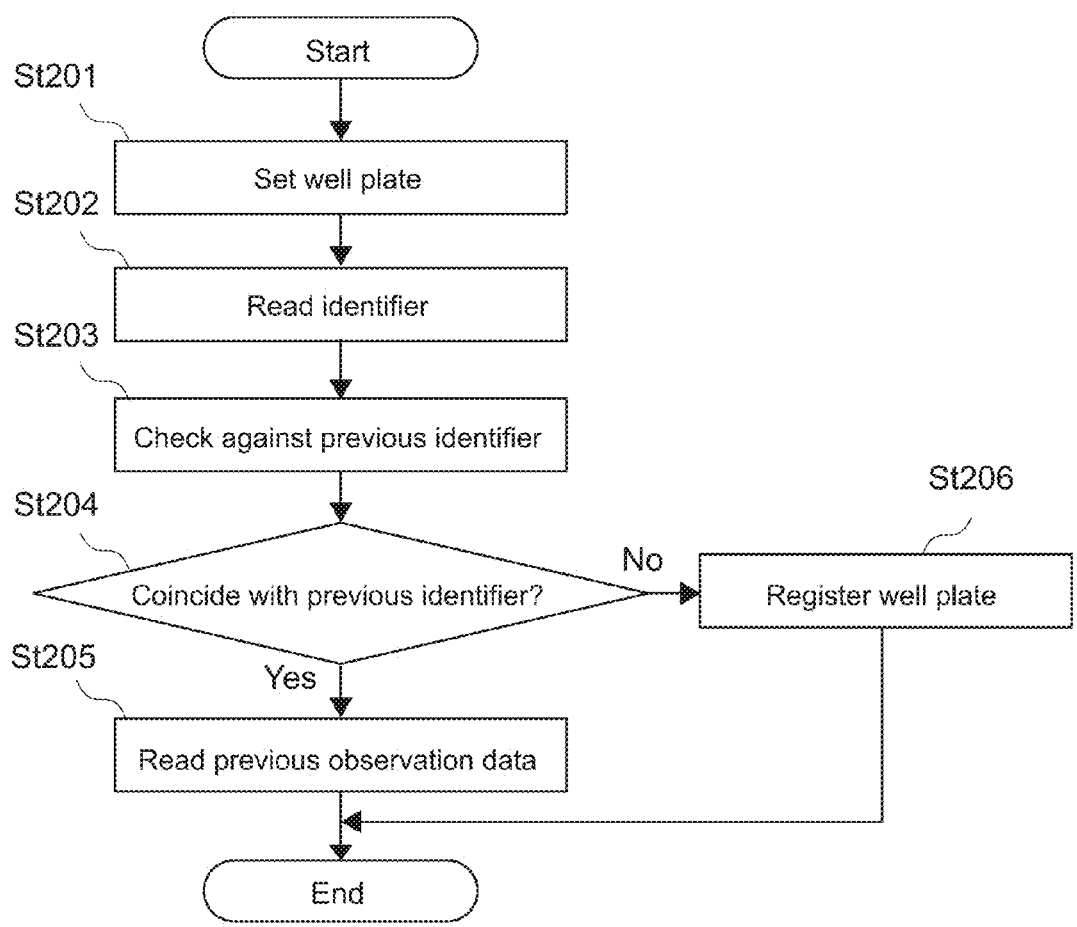
FIG. 8 is a flowchart showing an operation of the observation system.

FIG. 7 is a schematic diagram showing the observation system having a well plate identification function. In the observation system 100, the microscope unit 110 is further provided with an identifier read unit 119, and the control unit 120 further includes an identifier management unit 124.

The identifier read unit 119 reads an identifier from the identification marker provided to the well plate. The identifier read unit 119 is a camera or a barcode reader and is not particularly limited as long as the identifier read unit 119 can read the identifier. The identifier read unit 119 supplies the read identifier to the identifier management unit 124.

FIG. 9 is a flowchart showing an operation of the observation system having the well plate identification function. When the well plate is set to the incubator (St201), the stage 111 is driven, and the well plate is moved to an identifier read area along with the incubator. The identifier read unit 119 reads the identifier of the well plate (St202) and supplies the identifier to the identifier management unit 124.

The identifier management unit 124 checks the identifier supplied from the identifier read unit 119 against the identifier of the well plate which has been previously observed (St203). In the case where the supplied identifier coincides with the identifier of the well plate which has been previously observed (Yes in St204), the identifier management unit 124 reads observation data of the well plate which has been previously observed (St205). The observation data of the well plate which has been previously observed includes the observation target position and the observation target well (see, St105) from which the observation target object is detected by the detection unit 122 in the previous observation. The identifier management unit 124 supplies the read observation data to the image pickup control unit 121.

Thus, when the image pickup control unit 121 causes the image pickup unit 115 to take the detection image (St101), it is possible to exclude the well where the observation target object does not exist from the target the image of which is to be taken and cause the detection image to be taken mainly for the observation target position where the detection is performed in the previous observation.

In the case where the identifier supplied from the identifier read unit 119 does not coincide with the identifier of the well plate which has been previously observed (No in St204), the identifier management unit 124 registers the extracted identifier as a new well plate (St206). As a result, at a time when the well plate is observed in a subsequent observation, the image pickup control unit 121 can use the present observation data.

As described above, in the case where the observation system has the well plate identification function, the observation system can use the previous observation data for observation for each well plate. As a result, the observation system can exclude the well for which there is no need to perform the observation from the observation target and set the image-taking range on the basis of a three-dimensional position of the observation target object detected in the previous observation, with the result that the efficient observation can be performed.

It should be noted that the identifier read unit 119 does not necessarily have to read the identifier. The image pickup unit 115 can read the identifier from a microscope image taken through the microscope optical system 112. For example, in the case where the magnification of the microscope optical system 112 is 4×, the field-of-view range S is 2.2 mm×1.65 mm, so if the identification marker having this size or smaller is provided, it is possible to read the identifier from the microscope taken image. In addition, in the case where the magnification of the microscope optical system 112 is 2×—, it is possible to read the identification marker having a size of 4.4 mm×3.3 mm or smaller. That is, depending on the size of the identification marker, even in the case of the structure (structure shown in FIG. 1) to which the identifier management unit 119 is difficult to be provided, the identifier can be read.

It should be noted that the present disclosure can take the following configurations.

(1) An observation system, including:
a microscope optical system;
an image pickup unit configured to take an image of a field-of-view range of the microscope optical system;
an image pickup control unit configured to cause the image pickup unit to take images of an observation sample in the field-of-view range at a plurality of focal positions and generate detection images;
a detection unit configured to detect a three-dimensional position of an observation target object in the observation sample from the detection images; and
an observation control unit configured to fit the field-of-view range of the microscope optical system to the three-dimensional position.

(2) The observation system according to Item (1), in which
the image pickup control unit sets a magnification of the microscope optical system to a first magnification and causes the image pickup unit to take an image of the field-of-view range of the microscope optical system, and
the observation control unit sets the magnification of the microscope optical system to a second magnification higher than the first magnification and fits the field-of-view range of the microscope optical system to the three-dimensional position.

(3) The observation system according to Item (1) or (2), in which
the observation control unit causes the image pickup unit to take an image of the field-of-view range of the microscope optical system fitted to the three-dimensional position.

(4) The observation system according to any one of Items (1) to (3), further including
an ultraviolet, visible, and infrared light dispersion unit configured to disperse one of ultraviolet light, visible light, and infrared light incident from the microscope optical system, in which
the observation control unit causes the ultraviolet, visible, and infrared light dispersion unit to scan the field-of-view range of the microscope optical system fitted to the three-dimensional position.

(5) The observation system according to any one of Items (1) to (4), further including
a Raman scattering dispersion unit configured to disperse Raman scattering light incident from the microscope optical system, in which
the observation control unit causes the Raman scattering dispersion unit to scan the field-of-view range of the microscope optical system fitted to the three-dimensional position.

(6) The observation system according to any one of Items (1) to (5), in which
the observation sample is stored in each of a plurality of wells provided in a well plate, and
the observation target object is a cell seeded to each of the plurality of wells of the well plate.

(7) The observation system according to any one of Items (1) to (6), in which
the image pickup control unit registers the well, from which the observation target object is detected by the detection unit, as an observation target well along with the three-dimensional position of the observation target object, and excludes the well, from which the observation target object is not detected by the detection unit, from the observation target well.

(8) The observation system according to any one of Items (1) to (7), in which
the image pickup control unit performs a time-lapse image taking for the observation target well.

(9) The observation system according to any one of Items (1) to (8), further including:
an identifier read unit configured to read an identifier of the well plate from an identification marker provided to the well plate; and
an identifier management unit configured to check the identifier supplied from the identifier read unit against an identifier of a well plate which has been previously observed and supplies observation data of the well plate corresponding to the supplied identifier to the image pickup control unit.

(10) An observation program causing a computer to function as
an image pickup control unit configured to cause an image pickup unit that takes an image of a field-of-view range of a microscope optical system to take images of an observation sample in the field-of-view range at a plurality of focal positions and generate detection images,
a detection unit configured to detect a three-dimensional position of an observation target object in the observation sample from the detection images, and an observation control unit configured to fit the field-of-view range of the microscope optical system to the three-dimensional position.

(11) An observation method, including:

causing, by an image pickup control unit, an image pickup unit that takes an image of a field-of-view range of a microscope optical system to take images of an observation sample in the field-of-view range at a plurality of focal positions and generate detection images;

detecting a three-dimensional position of an observation target object in the observation sample from the detection images by a detection unit; and fitting the field-of-view range of the microscope optical system to the three-dimensional position by an observation control unit.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An observation system, comprising:
   a microscope optical system;
   an image pickup unit configured to take first images of a first field-of-view range of the microscope optical system within an observation range at a first plurality of focal positions and generate first detection images; if the first field-of-view range is smaller than the observation range, take second images of a second field-of-view range within the observation range at a second plurality of focal positions, and generate second detection images;
   an image pickup control unit configured to move the microscope optical system from the first field-of-view range to the second field-of-view range and cause the image pickup unit to take the first and second images and generate the first and second detection images at a first magnification;
   a detection unit configured to analyze each of the first and second detection images, detect an observation target object from the first and second detection images, supply a three-dimensional position of the observation target object to an observation control unit; and notify the image pickup control unit of the observation range if no observation target object is detected; and
   the observation control unit configured to adjust the microscope optical system to a third field-of-view range with a center corresponding to the three-dimensional position and cause the image pickup unit to take an image of the third field-of-view range at a second magnification higher than the first magnification.

2. The observation system according to claim 1, further comprising an ultraviolet, visible, and infrared light dispersion unit configured to disperse one of ultraviolet light, visible light, and infrared light incident from the microscope optical system, wherein the observation control unit is configured to cause the ultraviolet, visible, and infrared light dispersion unit to scan the third field-of-view range of the microscope optical system.

3. The observation system according to claim 1, further comprising a Raman scattering dispersion unit configured to disperse Raman scattering light incident from the microscope optical system, wherein the observation control unit is configured to cause the Raman scattering dispersion unit to scan the third field-of-view range of the microscope optical system.

4. The observation system according to claim 1, wherein the observation target object is a cell seeded to each of a plurality of wells provided in a well plate.

5. The observation system according to claim 4, wherein the image pickup control unit is configured to register the well, from which the observation target object is detected by the detection unit, as an observation target well along with the three-dimensional position of the observation target object, and exclude the well, from which the observation target object is not detected by the detection unit, from the observation target well.

6. The observation system according to claim 5, wherein the image pickup control unit is configured to perform a time-lapse image taking for the observation target well.

7. The observation system according to claim 6, further comprising:
   an identifier read unit configured to read an identifier of the well plate from an identification marker provided to the well plate; and
   an identifier management unit configured to check the identifier supplied from the identifier read unit against an identifier of a well plate which has been previously observed and supplies observation data of the well plate corresponding to the supplied identifier to the image pickup control unit.

8. A non-transitory computer-readable medium containing a computer program product causing a computer to function as an image pickup control unit configured to cause
   an image pickup unit to take first images of a first field-of-view range of a microscope optical system within an observation range at a first plurality of focal positions and generate first detection images at a first magnification; and if the first field-of-view range is smaller than the observation range, take second images of a second field-of-view range within the observation range at a second plurality of focal positions, and generate second detection images at the first magnification,
   a detection unit to analyze each of the first and second detection images, detect an observation target object from the first and second detection images, supply a three-dimensional position of the observation target object to an observation control unit and notify the image pickup control unit of the observation range if no observation target object is detected, and
   the observation control unit to adjust the microscope optical system to a third field-of-view range with a center corresponding to the three-dimensional position and cause the image pickup unit to take an image of the third field-of-view range at a second magnification higher than the first magnification.

9. An observation method, comprising:
   causing, by an image pickup control unit, an image pickup unit to take first images of a first field-of-view range of a microscope optical system within an observation range at a first plurality of focal positions and generate first detection images at a first magnification; and if the first field-of-view range is smaller than the observation range, take second images of a second field-of-view range within the observation range at a second plurality of focal positions, and generate second detection images at the first magnification;

detecting a three-dimensional position of an observation target object from the detection images by a detection unit;

adjusting the microscope optical system to a third field-of-view range with a center corresponding to the three-dimensional position by an observation control unit; and causing, by the observation control unit, the image pickup unit to take an image of the third field-of-view range of the microscope optical system at a second magnification higher than the first magnification.

* * * * *